United States Patent
Beuter et al.

(10) Patent No.: US 8,886,324 B2
(45) Date of Patent: Nov. 11, 2014

(54) METHOD AND APPARATUS FOR ELECTRICAL CORTEX STIMULATION

(75) Inventors: Anne Beuter, Merignac (FR); Julien Modolo, London (CA)

(73) Assignee: Centre National de la Recherche Scientifique-CNRS, Paris Cedex (FR)

( * ) Notice: Subject to any disclaimer, the term of this patent is extended or adjusted under 35 U.S.C. 154(b) by 346 days.

(21) Appl. No.: 13/320,177

(22) PCT Filed: Apr. 21, 2010

(86) PCT No.: PCT/EP2010/055252
§ 371 (c)(1), (2), (4) Date: Dec. 19, 2011

(87) PCT Pub. No.: WO2010/130538
PCT Pub. Date: Nov. 18, 2010

(65) Prior Publication Data
US 2012/0109252 A1    May 3, 2012

(30) Foreign Application Priority Data
May 14, 2009  (EP) .................................. 09305432

(51) Int. Cl.
*A61N 1/36* (2006.01)
*A61N 1/05* (2006.01)

(52) U.S. Cl.
CPC ........... *A61N 1/36082* (2013.01); *A61N 1/0531* (2013.01)
USPC .......................................................... 607/45

(58) Field of Classification Search
CPC ........... A61N 1/36003; A61N 1/36067; A61N 1/36082; A61N 1/3605; A61N 1/0531; A61N 1/36039; A61N 1/36064; A61N 1/36103

USPC ........................................................... 607/45
See application file for complete search history.

(56) References Cited

U.S. PATENT DOCUMENTS

| | | |
|---|---|---|
| 5,215,088 A | 6/1993 | Normann et al. |
| 2004/0088024 A1 | 5/2004 | Firlik et al. |
| 2006/0149337 A1 | 7/2006 | John |
| 2007/0142874 A1 | 6/2007 | John |
| 2009/0192569 A1* | 7/2009 | Llinas et al. .................... 607/45 |

FOREIGN PATENT DOCUMENTS

WO    WO 2010/130538 A1    11/2010

OTHER PUBLICATIONS

Atay and Hutt, SIAM J. Appl. Math., 2005, 65(2) 644-666.*
Ermentrout and Cowan, Biol. Cybern., 1979, 3, 137-150.*
International Search Report from corresponding PCT Application No. PCT/EP2010/055252 Report Dated Sep. 7, 2010.

* cited by examiner

*Primary Examiner* — Alyssa M Alter
(74) *Attorney, Agent, or Firm* — Miller, Matthias & Hull LLP (57) ABSTRACT

A method for cortex stimulation is disclosed which may include the steps of collecting electric signals by a control system from the cortex through an electrode array; determining signals by a virtual neural field having a virtual array corresponding the electrode array, the virtual array receiving the collected signals as an input and the virtual neural field being adapted to control the frequency spectrum of neural activity in the cortical target, each stimulation signal being determined by a value of the virtual potential at each point of the virtual array; and emitting the stimulation signals in the cortex through the electrode array.

18 Claims, 3 Drawing Sheets

METHOD AND APPARATUS FOR ELECTRICAL CORTEX STIMULATION

CROSS-REFERENCE TO RELATED APPLICATIONS

This application is a U.S. national stage filing of International Patent Application No. PCT/EP2010/055252 filed on Apr. 21, 2010, which claims priority under the Paris Convention to European Patent Application No. 09 305432.8, filed on May 14, 2009.

FIELD OF THE DISCLOSURE

1. Field of the Invention

The invention relates to methods and apparatuses for electrical stimulation of the cortex.

2. Background of the Disclosure

Electrical brain stimulation is a known method for treating a number of neurologic diseases, among which Parkinson's disease.

Electrical brain stimulation includes Deep Brain Stimulation (DBS) and Epidural Motor Cortex Stimulation (EMCS).

In DBS, electrodes are deeply implanted in the patient's brain, in the subthalamic nucleus, which requires a long and heavy surgical operation. An example of a DBS method is disclosed for instance in US-A-2008/046025 (Tass et al.).

In EMCS, on the contrary, electrodes are implanted superficially on the dura mater, which requires quicker and less invasive surgery, with less risk for the patient. An example of EMCS method is disclosed for instance by Franzini et al. (*Neurol. Res.* 2003; 25: 123-26).

The present invention relates more particularly to cortical stimulation (CS).

SUMMARY OF THE DISCLOSURE

One objective of the present invention is to improve the efficiency of known CS methods.

To this end, according to the invention, a method for CS is provided, in which an electrode array, having at least one electrode implanted in the cortex of a patient, eventually through the dura mater, is controlled by a control system, said method including at least the following steps:

(a) a measuring step wherein a number n of electric signals is collected by said control system from the cortex, each at a respective electrode of said electrode array, n being at least 1;

(b) a processing step wherein said control system determines n stimulation signals, by a virtual neural field having a virtual array of n points corresponding to each electrode of the electrode array having collected an electric signal at the measuring step (a), said virtual array receiving the collected signal as an input on each of the n points and said virtual neural field being adapted to control a frequency spectrum of neural activity in the cortex, each stimulation signal being determined by a value of said virtual potential at each virtual point of the virtual array;

(c) a stimulation step wherein said stimulation signals are emitted in the cortex by said control system, respectively at the electrodes of said electrode array corresponding respectively to the points of the virtual array.

Thanks to these dispositions:

implantation of the control system and electrode array does not require heavy surgery and is safer for the patient, due to the relatively superficial implantation of the electrode array;

the control system operates in a similar way as the cortex itself, the activity of which can also be modeled as a continuous neural field (see in particular Wilson and Cowan, *Kybernetik*, 1973, 13(2):55-80; and Amari, *Biol. Cybern.*, 1977, 27(2):77-87): this contributes to an operation of the control system which is closer to biological operation and therefore more efficient;

the control system operates in closed loop with the cortex, thus stimulating the cortex only when necessary, for instance only when tremor is present in the case of the treatment of Parkinson's disease: this results in minimal disturbance of the normal motor cortex activity, and in less power consumption by the control system which is of special importance when such control system is implanted and works on battery;

depending on the number of electrodes of the electrode array, the spatial resolution of the stimulation method may be high (and the stimulation is selective since all the electrodes are controlled individually), thus enabling to measure and stimulate the cortex activity at a mesoscopic scale corresponding to the scale of the electric waves in the cortex, which also results in better efficiency of the invention in such case.

In various embodiments of the method of the invention, one may possibly have recourse in addition to one and/or other of the following steps:

n is at least 50;

each collected signal and the corresponding stimulation signal are respectively collected and emitted in turn through the same electrode of the electrode array;

said electrode array has an electrode density of at least 4 electrodes/mm$^2$;

said electrode array covers a surface area comprised between 16 and 1000 mm$^2$ on the cortex;

said electrode array is implanted in the primary motor cortex;

said measuring step (a), processing step (b) and stimulation step (c) are cyclically reiterated;

said stimulating step (c) is carried out only if a triggering condition is satisfied by said collected signal at a triggering step (a') which takes place between said measuring step (a) and said stimulation step (c);

said triggering step (a') takes place between said measuring step (a) and said processing step (b), and said processing step (b) is carried out only if said triggering condition is satisfied;

at said triggering step (a'), the control system determines an amplitude of the collected signal for at least one predetermined frequency, and said triggering condition includes having said amplitude being larger than a predetermined threshold (such amplitude may be for instance the amplitude of the frequency spectrum of the collected signal in a certain bandwidth corresponding to said predetermined frequency);

the virtual neural field attenuates or augments neural activity in the cortex in a predetermined bandwidth;

the virtual neural field attenuates neural activity of the cortex in said predetermined bandwidth, which includes a target frequency of 10 Hz.

Another object of the present invention is an apparatus for cortical stimulation, comprising:

an electrode array including a number n of electrodes adapted to be implanted in the cortex of a patient, eventually through the dura mater, n being at least 1;

a control system controlling said electrode array, said control system being adapted to:

(a) collecting a number n of electric signals, each at a respective electrode of said electrode array;

(b) determining n stimulation signals, by a virtual neural field having a virtual array of n points corresponding to each electrode of the electrode array collecting said electric signals, said virtual array being configured to receive the collected signal as an input of each of the n points and said virtual neural field being adapted to control the frequency spectrum of neural activity in said cortex, each stimulation signal being determined by a value of said virtual potential at each point of the virtual array;

(c) emitting said stimulation signals in the cortex, respectively through the electrodes of said electrode array corresponding to the points of the virtual array.

In various embodiments of the apparatus of the invention, one may possibly have recourse in addition to one and/or other of the following arrangements:

n is at least 50;

the control system is adapted to respectively collect and emit in turn each collected signal and the corresponding stimulation signal through the same electrode of the electrode array;

said electrode array has an electrode density of at least 4 electrodes/mm$^2$;

said electrode array has a surface area comprised between 16 and 1000 mm$^2$;

the control system is adapted to cyclically reiterate measuring of the collected signals, determining the stimulation signals and emitting said stimulation signals;

the control system is adapted to emit said stimulating signals only if a triggering condition is satisfied by said collected signal;

the control system is adapted to determine an amplitude of the collected signal for at least one predetermined frequency, and said triggering condition includes having said amplitude being larger than a predetermined threshold (such amplitude may be for instance the amplitude of the frequency spectrum of the collected signal in a certain bandwidth corresponding to said predetermined frequency);

the virtual neural field is adapted to attenuate or augment neural activity of the cortex in a predetermined bandwidth;

the virtual neural field is adapted to attenuate neural activity of the cortex in said predetermined bandwidth, which includes a target frequency of 10 Hz.

BRIEF DESCRIPTION OF THE DRAWINGS

Other features and advantages of the invention appear from the following detailed description of one embodiment thereof, given by way of non-limiting examples, and with reference to the accompanying drawings.

In the drawings.

DETAILED DESCRIPTION OF THE DISCLOSURE

Figure 1:
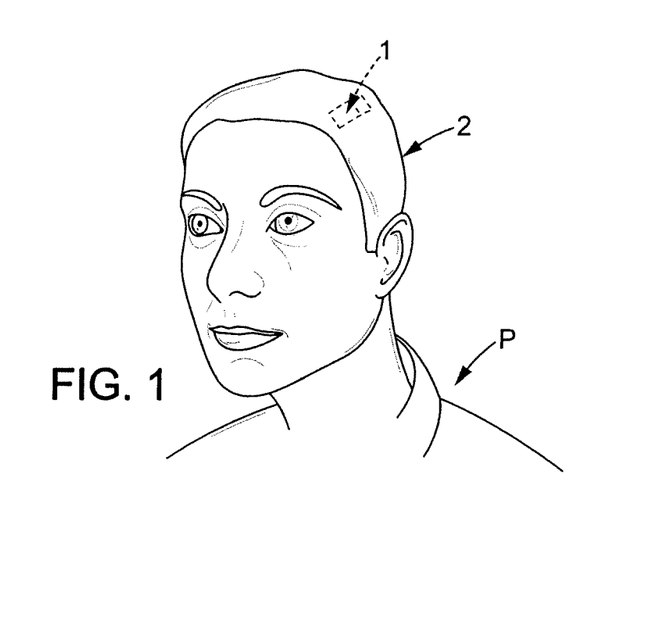
FIG. 1 is a diagrammatic view showing a possible implantation of an electrical stimulation apparatus in a patient's head, according to one embodiment of the invention.

As shown in FIG. 1, the present invention provides for a new electrical stimulation apparatus 1 which may be implanted in the head 2 of a human patient P, for carrying out Cortex Stimulation, i.e. for applying electrical stimuli in the cortex of the patient P. The electrical stimulation apparatus 1 may be used for instance for treating Parkinson's disease or other movement disorders such as essential tremor, dystonia or other neurological or neuropsychological disorders. In a variant, the electrical stimulation apparatus 1 might also be used for increasing the cortical activity in predetermined frequency bandwidths for cerebral augmentation purposes.

Figure 2:
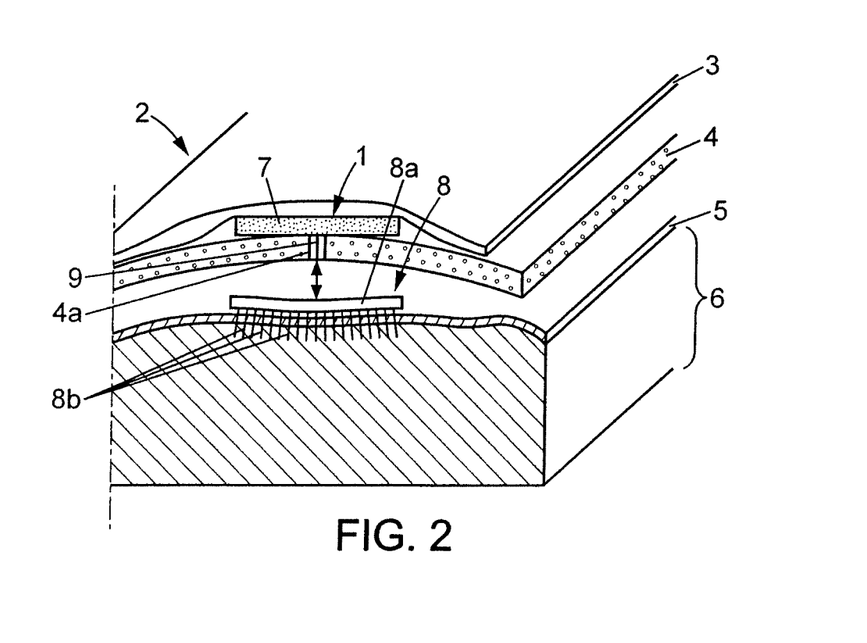
FIG. 2 is a detailed cutout view of the patient head, showing the electrical stimulation apparatus of FIG. 1.

As shown in FIG. 2, the head 2 of the patient includes skin 3 covering the skull 4. The skull 4 covers a thick membrane called the dura mater 5, which in turn covers the cortex 6, i.e. the superficial part of the brain. The electrical stimulation apparatus 1 may be implanted on any cortical target, for instance on a particular area of the brain called the primary motor cortex (generally referenced as the M1 zone), situated in the posterior portion of the frontal lobe of the brain.

As shown in FIG. 2, the electrical stimulation apparatus 1 may include for instance:

a control system 7 which may be implanted for instance between the skin 3 and the skull 4 of the patient's head 2;

an electrode array 8 which may be implanted between the skull 4 and the dura mater 5, or between the dura mater 5 and the cortex 6 in correspondence with any suitable part of the cortex 6, e.g. the primary motor cortex;

a connection 9—for instance a wire connection—between the central processing unit 7 and the electrode array 8.

The control system 7 is an electronic microcircuit fitted with a battery.

The electrode array 8 may include for instance:

a base plate 8a which is disposed between the skull 4 and the dura mater 5 or between the dura mater 5 and the cortex 6; the base plate 8a can be either rigid, or preferably in the form of a flexible mat;

and at least one electrode 8b, preferably a plurality of metal electrodes 8b which protrude downwardly from the base plate 8a toward the cortex 6 and may penetrate superficially in the cortex, eventually through the dura mater 5, so as to be in direct contact with the cortex.

As a variant, the electrical stimulation apparatus might be a unitary device including both the control system 7 and the electrode array in a single block which would then be located between the skull 4 and the dura mater 5, or between the dura mater 5 and the cortex 6.

The base plate 8a of the electrode array includes a micro circuit which connects the wire connection 9 to the electrodes 8b individually, so that said electrodes 8b be connected individually to the control system 7.

The electrode array 8 is implanted after trepanation of the patient, and a hole 4a is left in the skull 4 after surgery for the wire connection 9.

Figure 3:
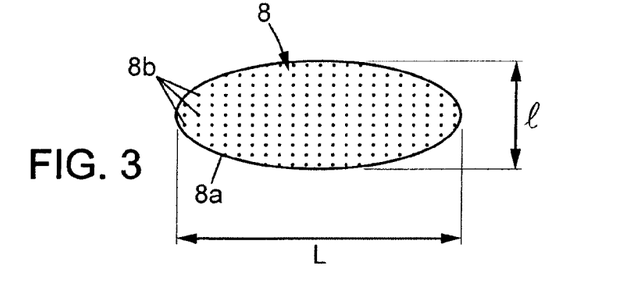
FIG. 3 shows an example of electrode array useable in the apparatus of FIG. 2.
Figure 4:
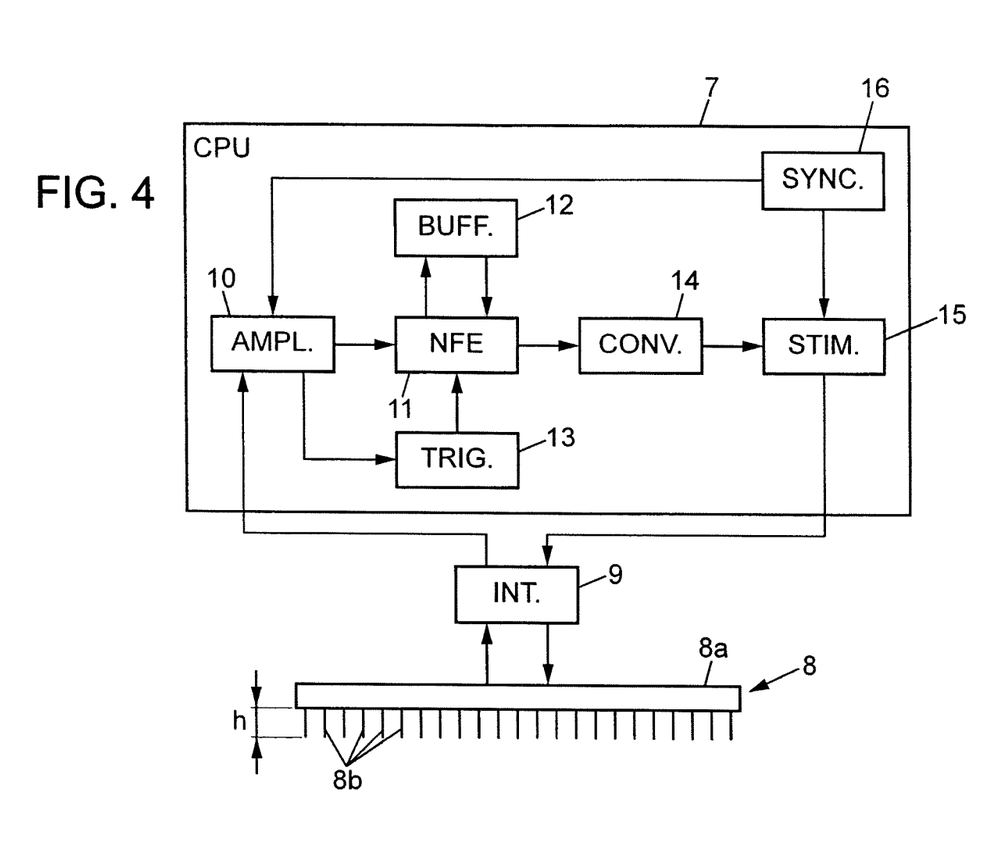
FIG. 4 is a block diagram of the electrical stimulation apparatus of FIG. 2.

As shown in FIGS. 3 and 4, the electrodes 8b may extend on a height h of a few millimeters from the base plate 8a, e.g. 1 to 3 mm. The electrode array 8 may include at least 50 electrodes 8b, preferably more than 100 electrodes, disposed on the base plate 8a at a density of at least 4 electrodes/mm$^2$ (e.g. 4 to 100 electrodes/mm$^2$, preferably 5 to 50 electrodes/mm$^2$). The base plate 8a may extend on a width 1 of a few millimeters (e.g. about 4 mm to about 1 cm) and a length L of a few millimeters (e.g. about 4 mm to a few cm), thus covering a surface area comprised between 16 mm² and a few cm² (e.g. 16 to 1000 mm², preferably 16 to 100 mm²) on the cortical tissue.

With the above electrode density of the electrode array 8, each electrode 8b corresponds to a neural mass of about 100 to 1000 neurons and is able to map part of the primary motor cortex at a mesoscopic scale. Therefore, the electrode array is well adapted to collect electric signals (voltages) from the cortex and send electric stimulation signals to the cortex with a good spatial resolution, and more especially with a spatial resolution which is of similar scale as the electric phenomena taking place in the cortex.

The electrode array may be similar to already existing electrode arrays used as brain implants, for instance "Utah" type electrode arrays marketed by Cybernetics Neurotechnology Systems Inc., USA.

The control system 7 (CPU) is shown on the block diagram of FIG. 4. The control system 7 can be an electronic autonomous microcircuit including a battery (not shown) and communicating with each electrode 8b of the electrode array 8 through the wire connection 9 (INT.) or through any other communication interface. The control system 7 includes the following modules, part of which can be either software or hardware modules:

- an amplifier 10 (AMPL.) for receiving and amplifying analogic electric signals collected by each electrode 8a, the amplifier also including analogic-numeric converters for sampling and converting all amplified collected signals in numeric form (the sampling rate may be for instance of about 1 kHz and the amplification may be such that the amplified collected signals have a maximum amplitude of e.g. 1V, the maximum amplitude of the collected signals being for instance of about 100 μV (microvolts) before amplification);
- a digital processor 11 (NFE) for receiving the amplified signals from the amplifier 10 and for solving a neural field equation which will be explained in details hereafter and for emitting electrical stimulation signals for each electrode 8b; the processor 11 receives the collected signals after amplification by amplifier 10; in a variant, the processor might be an analogic circuit (see in particular Zou et al., *Network: computation in Neural Sytems, Informa*, September 2006; 17(3): 211-233), in which case the collected signals may be sent in analogic form to the processor 11;
- a buffer 12 (BUFF.) connected to the processor 11 for storing past values of the collected signals;
- a triggering module 13 (TRIG.) which is connected to the output of amplifier 10 for performing frequency analysis of the collected signals; the triggering module 13 is connected to the processor 11 for inhibiting calculation of stimulation signals (or at least emission of such stimulation signals) by the processor 11 when the amplitude of the frequency spectrum of the collected signals does not exceed a predetermined threshold in a certain frequency range—for instance around 10 Hz (e.g. 8-12 Hz) in the case of the treatment of Parkinson's disease;
- a voltage—frequency converter 14 (CONV.) connected to the output of the processor 11 for converting the virtual potential signals transmitted by the processor into frequency signals values;
- a stimulation module 15 (STIM.) connected to the output of the converter 14 for transforming each frequency signal from the converter 14 into a series of voltage pulses having an instantaneous frequency corresponding to the frequency computed by the converter 14; the stimulation signals are transmitted by the stimulation parameter module to the corresponding electrodes 8b of the electrode array; said stimulation module 15 may also be adapted for managing the parameters of the electric stimulation (e.g., maximum frequency, amplitude, pulse width); this stimulation module may be activated by an outside apparatus (not shown) to adjust such parameters through a contactless link (e.g. by radio communication or by a communication through induction);
- a synchronizing module 16 (SYNC.), e.g. a clock, to guarantee that the reception of the collected signals from the electrodes 8b occurs at a different time from the transmission of the stimulation signals to the same electrodes (each electrode is used alternately to collect the signals from the cortex and to send the stimulation signals to the cortex).

The operation of the electric stimulation apparatus 1 will now be described.

This operation includes a cycle of 4 steps which are cyclically and continuously reiterated by the control system 7:

(a) a measuring step wherein a number n of electric signals is collected by said control system 7 from the cortex 6, each through a respective electrode 8b of said electrode array 8; in practice, n may be the number of electrodes 8b of the electrode array 8;

(a') a triggering step wherein the control system 7 (and more particularly the triggering module 13) determines the amplitude of the collected signal for at least one predetermined frequency (e.g. 10 Hz) and checks whether said amplitude is larger than a predetermined threshold (such amplitude may be for instance the amplitude of the frequency spectrum of the collected signal in a certain bandwidth corresponding to said predetermined frequency, e.g. 8-12 Hz): if it is larger, then the stimulation step (c) and possibly the processing step (b) may be inhibited and the process starts again at step (a), otherwise the process continues to step (b);

(b) a processing step wherein said control system determines n stimulation signals, by a virtual neural field having a virtual array of n points corresponding to each electrode of the electrode array having collected an electric signal at the measuring step (a), said virtual array receiving the collected signal as an input on each of the n points and said virtual neural field being adapted to control the frequency spectrum of neural activity in said cortical target, each stimulation signal being determined by a value of said virtual potential at each point of the virtual array;

(c) a stimulation step wherein said stimulation signals are emitted in the cortex by said control system, respectively through the electrodes of said electrode array corresponding respectively to points of the virtual array (each collected signal and the corresponding stimulation signal are respectively collected and emitted in turn through the same electrode of the electrode array).

When the invention is used for treating Parkinson's disease, the virtual neural field will be adapted to attenuate neural activity in the cortical target in a predetermined bandwidth in the low frequencies. This target bandwidth may include for instance a target frequency of 10 Hz and may range for instance from 8 to 12 Hz.

The equation of the continuous virtual neural field, which is solved by processor 11 in the control system 7, can be written as follows:

$$LV_a(x, t) = I(x, t) + \beta_a \int_\Omega W_a(d(x, y)) \cdot S\left[V_a\left(y, t - \frac{d(x, y)}{v}\right) - \theta\right] \cdot dy \quad (1)$$

wherein:

L is an operator equal to $$\lambda \cdot \frac{\partial^2}{\partial t^2} + \gamma \frac{\partial}{\partial t} + 1$$

(i.e.

$$LV(x, t) = \lambda \cdot \frac{\partial^2 V(x, t)}{\partial t^2} + \gamma \frac{\partial V(x, t)}{\partial t} + V(x, t);$$

in the example considered here, $\lambda$ may be for instance 0 and $\gamma$ may be for instance 1, so that $$LV(x, t) = \frac{\partial V(x, t)}{\partial t} + V(x, t));$$

$V_a$ is a potential in the virtual neural field (the index "a" stands for the virtual neural field hereafter), corresponding to a voltage, x is a spatial position in the virtual neural field (NB: in a 2D virtual neural field as considered here, x is a 2D vector);

t is time;

$\Omega$ is the spatial domain of the neural field (i.e. the surface area of the virtual array, corresponding to the surface area of the electrode array);

d(x,y) is the distance between two spatial positions x, y in the spatial domain $\Omega$;

v is the propagating speed of the signal in the virtual neural field;

$\beta_a$ is the synaptic strength in the virtual neural field;

$W_a(d(x,y))$ is the connectivity kernel of the virtual field, i.e. the probability that the neural masses at positions x and y be synaptically connected;

S(V) is a sigmoid function which provides a correspondence between the potential V and the corresponding firing rate of the neurons (i.e. a potential value V is transformed into an electric discharge frequency);

$\theta$ is the firing threshold;

I(x,t) is an external input: here, I(x,t) is a function of the electric signals $V_r(x,t)$ collected through the electrodes 8b (the index "r" stands for the real neural field hereafter, i.e. the cortical neural field) and applied to the points of the virtual array in the virtual neural field.

In the example considered here, the following formulas may be used for I, W and S:

$$I(x, t) = \beta_{ar} \cdot \int_\Omega \cdot W_{ar}(d(x, y)) \cdot S[V_r(y, t - \tau_{ar}) - \theta] \cdot dy \quad (1a)$$

$$W(d(x, y)) = \frac{1}{\sqrt{\pi}} [a_e \exp(-d(x, y)^2 - a_i r \exp(-r^2 d(x, y)^2)] \quad (1b)$$

(see Atay and Hutt, *SIAM J. Appl. Math.*, 2005, 65(2):644-666; formula (1b) may be used for all connectivity kernels mentioned here, to wit $W_r$, $W_a$, $W_{ar}$, $W_{ra}$);

$$S(V) = \frac{f_{max}}{1 + \exp[-\lambda(V - \theta)]} \quad (1c)$$

where:

$\beta_{ar}$ is the synaptic strength between the real and the virtual neural fields;

$W_{ar}$ is the connectivity kernel between the real and the virtual neural fields, i.e. the probability that neural masses respectively at positions x and y respectively in the real and virtual fields be synaptically connected;

$$\tau_{ar} = \frac{d(x, y)}{v}$$

is a delay;

$a_e/a_i$ are the excitatory/inhibitory synaptic weights respectively; and r is the ratio of spatial ranges between excitatory and inhibitory fibers;

$f_{max}$ is the maximum discharge rate of the neurons in the neural field;

$\lambda$ is a non-dimensional parameter.

In the example considered here, typical values of the above parameters may be as follows:

$f_{max}$: about 100 Hz;

v: about 1 m/s;

$\theta$: about 3 mV;

$\beta_a$, $\beta_r$, $\beta_{ra}$, $\beta_{ar}$: about 2;

$a_e$: about 50;

$a_i$: about 30;

r: about 0.5.

Based on the above equations (1) to (1c) and on the measured electric signals $V_r(x,t)$, the processor 11 computes values of the virtual potential $V_a(x,t)$ for each point of the virtual area corresponding to the electrode 8b of the electrode array 8 at which $V_r(x,t)$ was measured.

Each virtual potential $V_a(x,t)$ corresponding to each point of the virtual array is then converted by the converter 14 into a stimulation frequency $f_s(x)$ which is given by the sigmoid function S(V(x,t)) mentioned above.

Then, each stimulation frequency $f_s(x)$ is converted into a series of pulses by the stimulation parameter module which shapes the stimulation signals E(x,t) in amplitude, pulse width and maximum pulse frequency ($f_0 = 1/T_0$, where $T_0$ is the total time between the beginning of two consecutive pulses of the same stimulation signal E(x,t)). The stimulation parameter module then transmits the stimulation signal E(x,t) to the corresponding electrodes 8b of the electrode array 8 to enable emission thereof in the cortex 6. In the example considered here, all stimulation signals E(x,t) may have the same maximum frequency $f_0$, amplitude and pulse width, and the stimulation signals E(x,t) sent simultaneously to the various electrodes 8b differ from each other by the number of pulses emitted during the time frame allotted to transmission of the stimulation signals. For instance, the amplitude of the pulses may be of about 1V and the pulse width may be of about 50 to 150 µs (microseconds), preferably about 60 to 90 µs. The pulse maximum frequency $f_0$ may be for instance in the range 300-500 Hz.

The stimulation module 15 may transmit the stimulation signals with a predetermined delay $\tau$, which is at least 50 µs after the recording period because of the processing by the control system 7. Such delay is compatible with a real-time functioning of the invention, appropriate for the control of a biological system.

Between consecutive recording periods, stimulation signals are transmitted to the electrode array 8 if the triggering condition of module 13 is fulfilled.

The efficiency of the invention for creating a closed loop between the cortex and the virtual neural field can be explained when considering that the cortex itself functions as a continuous neural field. Indeed neural field models have successfully explained and predicted cortical phenomena such as travelling waves and visual patterns during hallucinations (see in particular Ermentrout and Cowan, *Biol. Cybern.*, 1979, 3:137-150). Then, the equation of this real neural field may be expressed as follows:

$$LV_r(x,t) = E(x,t) + \beta_r \int_\Omega W_r(d(x,y)) \cdot S\left[V_r\left(y, t - \frac{d(x,y)}{v}\right) - \theta\right] \cdot dy \quad (2)$$

wherein:
- L is the operator already defined for equation (1);
- $V_r$ is the mean potential in the real neural field, corresponding to a voltage in the real neural field of the cortex (i.e., the cortical target),
- x is a spatial position in the real neural field (NB: in a 2D virtual neural field as considered here, x is a 2D vector);
- t is time;
- $\Omega$ is the spatial domain of the neural field (i.e. the surface area of the virtual array, corresponding to the surface area of the electrode array);
- d(x,y) is the distance between two spatial positions x, y in the spatial domain $\Omega$;
- v is the propagating speed of the signal in the real neural field;
- $\beta_r$ is the synaptic strength in the real neural field;
- $W_r(d(x,y))$ is the connectivity kernel of the real neural field, i.e. the probability that the neural masses at positions x and y be synaptically connected;
- S(V) is a sigmoid function which provides a correspondence between the potential V and the corresponding firing rate of the neurons (i.e. a potential value is transformed into an electric discharge frequency); S may be expressed for instance by the above formula (1c);
- $\theta$ is the firing threshold;
- E(x,t) is the electric stimulation coming from the stimulation apparatus 1.

The electric stimulation E(x,t) depends upon the potential V throughout the neural field:

$$E(x,t) = \int_\Omega \zeta[V_r(y, t-\tau)] \cdot dy \quad (3)$$

where $\zeta[V_r(y,t-\tau)]$ is an unknown function and where $$\tau = \frac{d(x,y)}{v}$$

is a delay. Although this function is unknown, it may be rewritten in the following form, supposing that the virtual neural field behaves like the real cortical network, i.e., the virtual neural field is described by the same equation as the cortical target:

$$\zeta[V_r(y,t-\tau)] = \beta_{ra} \cdot W_{ra}(d(x,y)) \cdot S[V_a(y, t-\tau_{ra}) - \theta] \quad (4)$$

where $\beta_{ra}$ is the synaptic strength between the virtual and the real neural field and $W_{ra}$ is the connectivity kernel between the virtual and the real neural fields, i.e. the probability that neural masses respectively at positions x and y respectively in the virtual and real fields be synaptically connected.

When bringing equation (4) in equation (2), one obtains equation (5):

$$LV_r(x,t) = \beta_{ra} \int_\Omega W_{ra}(d(x,y)) \cdot S[V_a(y, t-\tau_{ra}) - \theta] \cdot dy + \quad (5)$$
$$\beta_r \int_\Omega W_r(d(x,y)) \cdot S\left[V_r\left(y, t - \frac{d(x,y)}{v}\right) - \theta\right] \cdot dy$$

As already explained above, the equation of the virtual neural field can be written in a similar form (6):

$$LV_a(x,t) = \beta_{ar} \int_\Omega W_{ar}(d(x,y)) \cdot S[V_r(y, t-\tau_{ar}) - \theta] \cdot dy + \quad (6)$$
$$\beta_a \int_\Omega W_a(d(x,y)) \cdot S\left[V_a\left(y, t - \frac{d(x,y)}{v}\right) - \theta\right] \cdot dy$$

Therefore, the coupling between the virtual neural field and the real neural field can be modelled by the two coupled integro-differential equations (5) and (6).

The parameters of the virtual neural field are adapted to obtain the desired control of the frequency spectrum of the cortical target, and therefore the frequency spectrum of the real potential (voltage) signals in the cortex, in order to attenuate the cortical activity at certain frequencies (to alleviate a disorder) or to increase such cortical activity at certain frequencies (e.g., for sensory augmentation purposes). For instance, in the treatment of Parkinson's disease, it will be suitable to attenuate the potential signals in a predetermined bandwidth in the low frequencies (e.g. around 10 Hz, for instance in the target bandwidth 8-12 Hz as mentioned above).

Two possible approaches may be used to set these parameters.

A. The first approach consists in an analytical study of the system formed by the two neural field equations (5) and (6) (one for the virtual neural field of the stimulation apparatus 1, one for real neural field of the cortical target). The different steps in this first approach may be summarized as:
1) computing the equilibrium state of the system;
2) writing down the linearized equations around the equilibrium to obtain the expression of the mean potential in response to small external inputs;
3) computing the Green function of the cortical target, i.e., the response function to external inputs;
4) using the Green function to compute the auto-correlation function of the potential;
5) using the Wiener-Khinchin theorem stating that the power spectrum is the Fourier transform of the auto-correlation function; and
6) obtaining an analytical expression of the power spectrum of neuronal activity in the neuronal target depending on the parameters of the virtual array. Consequently, depending on the frequency band to be attenuated (to alleviate a disorder) or increased (e.g., for sensory augmentation purposes), parameter values may be chosen from the analytical expression of the power spectrum.

B. The second approach consists in a numerical study of the system formed by two neural field equations (5) and (6). To do so, both neural field equations are solved using a numerical method such as for instance Euler's method or fourth-order Runge-Kutta's method. As a result, potential values are computed at each point of space and time for both the cortical target and the virtual array. A spectrogram (i.e., a time-frequency analysis) of the computed potential in the cortical target gives the power spectrum of neuronal activity depending on the parameters of the virtual array. Thus, it is possible to investigate, depending on parameters of the virtual array, which frequency bands are decreased (for therapeutic purpose) or increased (for augmentation purpose). Several theoretical results exist to guide such numerical studies. For instance, the more general distance-dependent connectivity kernel used in neural field models is (see in particular Atay and Hutt, *SIAM J. Appl. Math.*, 2005, 65(2):644-666):

$$W(z) = \frac{1}{\sqrt{\pi}} [a_e \exp(-z^2) - a_i \times r \times \exp(-r^2 z^2)]$$

where:
 z is the distance between two points in the neural field;
 $a_e/a_i$ are the excitatory/inhibitory synaptic weights respectively, and
 r is the ratio of spatial ranges between excitatory and inhibitory fibers.

Analytical studies, (see for example Atay and Hutt, *SIAM J. Appl. Math.*, 2005, 65(2):644-666 showed that, depending on the form of W(z), different neuronal activity patterns could be observed. For instance, it is known that a locally excitatory/lateral inhibitory ($a_e > a_i > 0$ and $r > 1$) connectivity kernel allows both stationary and propagating waves of neuronal activity throughout the cortex. Consequently, with guidelines from analytical study of neural fields equations, it is possible to determine appropriate parameter values for efficient cortical target control using numerical simulations.

SIMPLIFIED EXAMPLE

One simplified example of the invention, in which space is not taken into account (i.e. equivalent to using an electrode array with a single electrode 8b), has been carried out by numerical simulation. In this example, the real neural field is considered to include both an excitatory population (index E) and an inhibitory population (index I). Without control, the excitatory population creates a strong pathological 5 Hz activity (typically occurring during Parkinson's disease in the subthalamic nucleus). The stimulation of the virtual population (index A) of the virtual neural field is provided to the excitatory population E and the evolution of both real and virtual neural fields is described by the two coupled equations (7) and (8) (only the potential of the excitatory population E is mentioned hereafter as far as the real neural field is concerned):

$$\tau_E \frac{dV_E}{dt} + V_E = aS_E(V_E) - bS_E(V_E) - eS_I(V_A) \quad (7)$$

$$\tau_A \frac{dV_A}{dt} + V_A = fS_E(V_E) \quad (8)$$

In this example, $\tau_E = \tau_A = 6$ ms (milliseconds) are the membrane time constants of the two neural fields; a=0.05; b=0.1; e=f=0.05 (a, b, e, f are non-dimensional synaptic weights); and $S_E$, $S_I$, $S_A$, are the sigmoid functions of the three populations.

Figure 5:
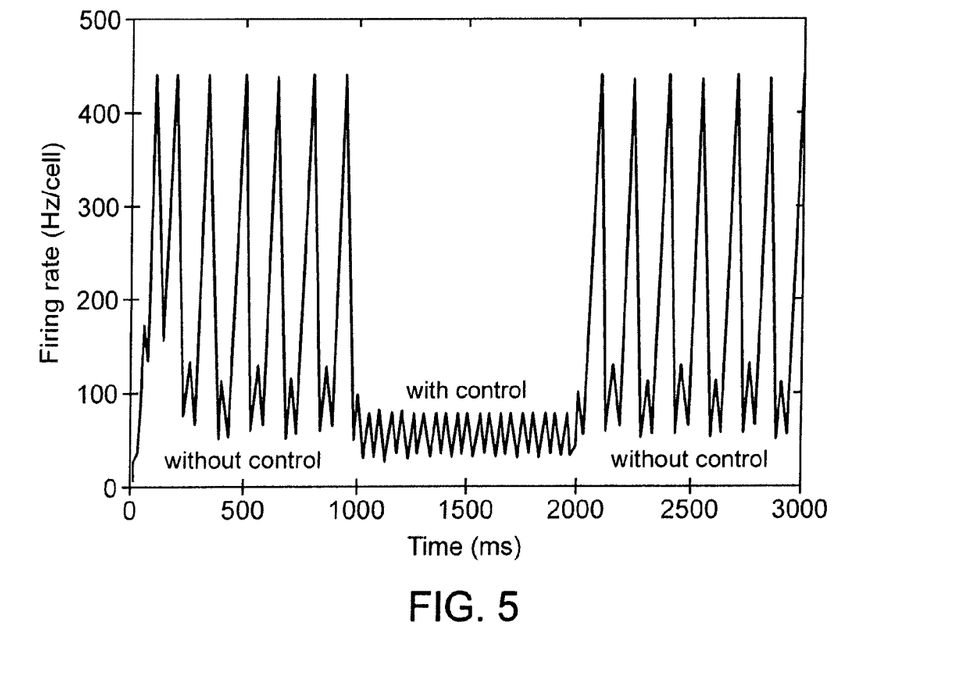
FIG. 5 is a diagram showing a simulation of the activity of a neural mass of the cortex as a function of time, with and without control by the electrical stimulation apparatus according to the invention.

FIG. 5 shows a diagram of simulated electrical signals in the cortex in this example, showing the amplitudes of the electric signals as a function of time. The amplitude of the signals is represented by the firing rate of the neurons in Hz/cell. FIG. 5 show that the stimulation signals emitted according to the invention are efficient to control the 5 Hz, high amplitude signals.

The invention claimed is:
1. A method for determining stimulation signals in a cortical stimulation apparatus in which an electrode array, having at least one electrode adapted to be implanted in the cortex of a patient, is controlled by a control system, said method including at least the following steps:
 (a) a measuring step wherein a number n of electric signals is collected by said control system, each at a respective electrode of said electrode array, n being at least 1;
 (b) a processing step wherein said control system determines n stimulation signals, by a virtual neural field having a virtual array of n points corresponding to each electrode of the electrode array having collected an electric signal at the measuring step, said virtual array receiving the collected signal as an input on each of the n points and said virtual neural field being adapted to control the frequency spectrum of neural activity in the cortex, each stimulation signal being determined by a value of said virtual potential at each point of the virtual array using the following formula:

$$LV_a(x,t) = I(x,t) + \beta_a \int_\Omega W_a(d(x,y)) \cdot S\left[V_a\left(y, t - \frac{d(x,y)}{v}\right) - \theta\right] \cdot dy \quad (1)$$

where:
 L is an operator equal to $$\lambda \cdot \frac{\partial^2}{\partial t^2} + \gamma \frac{\partial}{\partial t} + 1;$$

$V_a$ is a potential in the virtual neural field;
 x is a spatial position in the virtual neural field;
 t is time;
 $\Omega$ is a spatial domain of the neural field;
 d(x,y) is a distance between two spatial positions x, y in the spatial domain $\Omega$;
 v is a propagating speed of a signal in the virtual neural field;
 $\beta_a$ is a synaptic strength in the virtual neural field;
 $W_a(d(x,y))$ is a connectivity kernel of the virtual field;
 S(V) is a sigmoid function which provides a correspondence between a potential V and a corresponding firing rate of neurons;
 $\theta$ is a firing threshold; and
 I(x,t) is a function of the electric signals $V_r(x,t)$ collected through the electrodes (8b) and applied to the points of the virtual array in the virtual neural field, wherein:

$$I(x,t) = \beta_{ar} \cdot \int_\Omega \cdot W_{ar}(d(x,y)) \cdot S[V_r(y, t - \tau_{ar}) - \theta] \cdot dy \quad (1a)$$

$$W(d(x,y)) = \frac{1}{\sqrt{\pi}} [a_e \exp(-d(x,y)^2 - a_i r \exp(-r^2 d(x,y)^2)] \quad (1b)$$

$$S(V) = \frac{f_{max}}{1 + \exp[-\lambda(V - \theta)]} \quad (1c)$$

where:
$\beta_{ar}$ is a synaptic strength between the real and the virtual neural fields;
$W_{ar}$ is a connectivity kernel between the real and the virtual neural fields;

$$\tau_{ar} = \frac{d(x, y)}{v}$$

is a delay;
$a_e/a_i$ are an excitatory/inhibitory synaptic weights respectively;
r is a ratio of spatial ranges between excitatory and inhibitory fibers;
$f_{max}$ is a maximum discharge rate of neurons in the neural field; and
$\lambda$ is a non-dimensional parameter;
(c) a stimulation step wherein said stimulation signals are emitted by said control system, respectively at the electrodes of said electrode array corresponding respectively to the points of the virtual array.

2. The method according to claim 1, wherein n is at least 50 and said electrode array has an electrode density of at least 4 electrodes/mm$^2$.

3. The method according to claim 1, wherein each collected signal and the corresponding stimulation signal are respectively collected and emitted in turn through the same electrode of the electrode array.

4. The method according to claim 1, wherein said measuring step, processing step and stimulation step are cyclically reiterated.

5. The method according to claim 1, wherein said stimulating step is carried out only if a triggering condition is satisfied by said collected signal at a triggering step which takes place between said measuring step and said stimulation step.

6. The method according to claim 1, wherein at said triggering step, the control system determines an amplitude of the collected signal for at least one predetermined frequency, and said triggering condition includes having said amplitude being larger than a predetermined threshold.

7. The method according to claim 1, wherein the virtual neural field is adapted to attenuate or augment the neural activity of the cortex in a predetermined bandwidth.

8. The method according to claim 1, wherein the virtual neural field is adapted to attenuate neural activity of the cortex in said predetermined bandwidth, which includes a target frequency of 10 Hz.

9. An apparatus for cortex stimulation, comprising:
an electrode array including a number n of electrodes adapted to be implanted in the cortex of a patient, n being at least 1; a control system controlling said electrode array, said control system being adapted to:
(a) collecting a number n of electric signals, each at a respective electrode of said electrode array;
(b) determining n stimulation signals, by a virtual neural field having a virtual array of n points corresponding to each electrode of the electrode array collecting said electric signals, said virtual array being configured to receive the collected signal as an input on each of the n points and said virtual neural field being adapted to control the frequency spectrum of neural activity in the cortex, each stimulation signal being determined by a value of said virtual potential at each point of the virtual array using the following formula:

$$LV_a(x, t) = I(x, t) + \beta_a \int_\Omega W_a(d(x, y)) \cdot S\left[V_a\left(y, t - \frac{d(x, y)}{v}\right) - \theta\right] \cdot dy \quad (1)$$

where:
L is an operator equal to $$\lambda \cdot \frac{\partial^2}{\partial t^2} + \gamma \frac{\partial}{\partial t} + 1;$$

$V_a$ is a potential in the virtual neural field;
x is a spatial position in the virtual neural field;
t is time;
$\Omega$ is a spatial domain of the neural field;
d(x,y) is a distance between two spatial positions x, y in the spatial domain $\Omega$;
v is a propagating speed of a signal in the virtual neural field;
$\beta_a$ is a synaptic strength in the virtual neural field;
$W_a(d(x,y))$ is a connectivity kernel of the virtual field;
S(V) is a sigmoid function which provides a correspondence between a potential V and a corresponding firing rate of neurons;
$\theta$ is a firing threshold; and
I(x,t) is a function of the electric signals $V_r(x,t)$ collected through the electrodes (8b) and applied to the points of the virtual array in the virtual neural field, wherein:

$$I(x, t) = \beta_{ar} \cdot \int_\Omega \cdot W_{ar}(d(x, y)) \cdot S[V_r(y, t - \tau_{ar}) - \theta] \cdot dy \quad (1a)$$

$$W(d(x, y)) = \frac{1}{\sqrt{\pi}} [a_e \exp)(-d(x, y)^2 - a_i r \exp(-r^2 d(x, y)^2)] \quad (1b)$$

$$S(V) = \frac{f_{max}}{1 + \exp[-\lambda(V - \theta)]} \quad (1c)$$

where:
$\beta_{ar}$ is a synaptic strength between the real and the virtual neural fields;
$W_{ar}$ is a connectivity kernel between the real and the virtual neural fields;

$$\tau_{ar} = \frac{d(x, y)}{v}$$

is a delay;
$a_e/a_i$ are an excitatory/inhibitory synaptic weights respectively;
r is a ratio of spatial ranges between excitatory and inhibitory fibers;
$f_{max}$ is a maximum discharge rate of neurons in the neural field; and
$\lambda$ is a non-dimensional parameter;

(c) emitting said stimulation signals in the cortex, respectively at the electrodes of said electrode array corresponding to the points of the virtual array.

10. The apparatus according to claim 9, wherein n is at least 50.

11. The apparatus according to claim 9, wherein the control system is adapted to respectively collect and emit in turn each collected signal and the corresponding stimulation signal through the same electrode of the electrode array.

12. The apparatus according to claim 9, wherein said electrode array has an electrode density of at least 4 electrodes/$mm^2$.

13. The apparatus according to claim 9, wherein said electrode array has a surface area comprised between 16 and 1000 $mm^2$.

14. The apparatus according to claim 9, wherein the control system is adapted to cyclically reiterate measuring of the collected signals, determining the stimulation signals and emitting said stimulation signals.

15. The apparatus according to claim 9, wherein the control system is adapted to emit said stimulating signals only if a triggering condition is satisfied by said collected signal.

16. The apparatus according to claim 9, wherein the control system is adapted to determine an amplitude of the collected signal for at least one predetermined frequency, and said triggering condition includes having said amplitude being larger than a predetermined threshold.

17. The apparatus according to claim 9, wherein the virtual neural field is adapted to attenuate or augment neural activity of the cortex in a predetermined bandwidth.

18. The apparatus according to claim 9, wherein the virtual neural field is adapted to attenuate neural activity of the cortex in said predetermined bandwidth, which includes a target frequency of 10 Hz.

* * * * *